US00PP29743P2

(12) United States Plant Patent
Korlipara

(10) Patent No.: US PP29,743 P2
(45) Date of Patent: Oct. 9, 2018

(54) ***ECHINACEA* PLANT NAMED 'TNECHKRD'**

(50) Latin Name: ***Echinacea* spp.**
Varietal Denomination: TNECHKRD

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 15/731,244

(22) Filed: May 9, 2017

(51) Int. Cl.
*A01H 5/02* (2018.01)

(52) U.S. Cl.
USPC ..... Plt./428

(58) Field of Classification Search
USPC ..... Plt./428
See application file for complete search history.

*Primary Examiner* — Keith O. Robinson
(74) *Attorney, Agent, or Firm* — Klarquist Sparkman, LLP

(57) ABSTRACT

A new and distinct *Echinacea* plant named 'TNECHKRD' characterized by an amazing number of inflorescences starting in the first season, very long bloom time with excellent rebloom, very upright, compact habit, deep red ray florets surrounding dark cones, numerous, strong stems, and excellent vigor.

1 Drawing Sheet

Botanical denomination: *Echinacea* spp.
Variety designation: 'TNECHKRD'.

BACKGROUND OF THE INVENTION

The present invention relates to a new and distinct cultivar of *Echinacea* and given the cultivar name 'TNECHKRD'. *Echinacea* is in the family Asteraceae. The new cultivar is part of a planned breeding program for a landscape series with compact habits and profuse inflorescences. The exact parents of this selection are unknown, unnamed, proprietary interspecific hybrids bred from *Echinacea paradoxa, Echinacea purpurea,* and *Echinacea tennesseensis.*

Compared to *Echinacea* 'Dixie Scarlet', U.S. Plant Pat. No. 26,110, the new cultivar is shorter with deeper red ray florets.

Compared to *Echinacea* 'Balsomsed', U.S. Plant Pat. No. 23,105, the new cultivar has larger, flatter inflorescences and a deeper red ray floret.

This new *Echinacea* cultivar is uniquely distinguished by:

1. an amazing number of inflorescences starting in the first season,
2. very long bloom time with excellent rebloom,
3. very upright, compact habit,
4. deep red ray florets surrounding dark cones,
5. numerous, strong stems, and
6. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a close up of the inflorescences of *Echinacea* 'TNECHKRD' on a nine-month-old plant growing in the trial field in full sun in late June in Canby, Oreg.

FIG. 2 shows the habits of the nine-month-old *Echinacea* 'TNECHKRD' in bloom in the field in early July in full sun in Canby, Oreg.

DETAILED PLANT DESCRIPTION

The following is a detailed description of the new *Echinacea* cultivar based on observations of seven-month-old specimens growing in the trial field in full sun in Canby, Oreg. Canby is in Zone 8 on the USDA Hardiness map. Temperatures range from a high of 95° F. in August to an average of 32° F. in January. Normal rainfall in Canby is 42.8 inches per year in the trial fields in Canby, Oreg. The color descriptions are all based on The *Royal Horticultural Society Colour Chart,* 5$^{th}$ edition, 2007.

Plant:

*Type.*—Herbaceous perennial.
*Hardiness.*—USDA Zones 4 to 9.
*Size.*—Grows to about 40 cm wide and 47 cm tall to top of inflorescences.
*Form.*—Basal clump, with about 13 stems from the base.
*Vigor.*—Excellent.
*Roots.*—Fibrous, with many downward growing and few laterals, ivory in color, Yellow White 158D, roots develop easily from cuttings from the crown.

Leaf (stem):

*Type.*—Simple.
*Shape.*—Lanceolate.
*Arrangement.*—Alternate.

*Leaf number*.—Up to 15.

*Blade size*.—Grows to 14 cm long and 3.4 cm wide.

*Margins*.—Entire.

*Apex*.—Acuminate.

*Base*.—Attenuate.

*Surface texture*.—Strigose on both sides.

*Rugosity*.—Weak.

*Venation*.—Pinnate, Yellow Green 147C on both sides.

*Color*.—Topside Green N137A, bottom side closest to Yellow Green 147A.

*Variegation*.—Absent.

*Petiole description*.—Clasping, grows to 4 cm long and 4 mm wide, scabrous, narrow leafy edges which fold upwards, topside Yellow Green 147B in middle with leafy Green N137B edges, bottom side closest to Yellow Green 147B.

Inflorescence:

*Type*.—Composite on terminal stalked heads.

*Number of flowering stems from the ground*.—About 13.

*Flowering stem*.—Grows to 43 cm tall from the base of the plant to the terminal inflorescence and can grow to 19 cm long from the top stem leaf to the base of an inflorescence; unbranched to branched, with 1 to 4 inflorescences per stem; diameter growing to 9 mm wide near the inflorescence; strigose, strong; Yellow Green 147C tinted 177B in sun.

*Size*.—Grows to 9.5 cm wide and 5 cm deep as disc enlarges.

*Form*.—Ray florets held horizontally, mature disc is conic.

*Immature inflorescence*.—3.5 cm wide and 2.5 cm deep, ray florets held upright at a 50 degrees angle and rolled up so only the back color shows, Greyed Purple N186D, disc color Yellow Green 144A in center ½ to Brown 200B outside ½.

*Ray florets*.—Without pistil or stamen, 24 to 34 in number, grow to 43 mm long and 13 mm wide, oblanceolate with the tip two-to three-toothed (each acute), entire margins, base attenuate, glabrous on both sides; topside Red 46A, bottom side Red Purple 31A; aging to (when disc florets full open) topside Red 46A on bottom ⅓ and up middle blending to Greyed Orange 170B; twisting of ray florets — absent.

*Disc*.—Daisy type, flat becoming conic, becoming 45 mm deep and 44 mm wide with maturity, Greyed Purple 187A in background with bracts Greyed Orange 176B with tips Greyed Purple 187A.

*Disc florets*.—To about 450 in number, each with 1 pistil and 4 stamen, grow to 10 mm long and 2.5 mm wide, each with one persistent, very stiff linear bract (14 mm long with the tip Greyed Purple 187A to 4 mm Greyed Purple N186D blending to 4 mm Yellow Green 147C blending to White NN155A on bottom); corolla 6 mm long and 2 mm wide, tubular, 5 lobed, glabrous, Greyed Purple 187B with lobe tips 187A; pistil 10 mm long, ovary 4 mm long, White NN155D with top Yellow Green 144A, style 5 mm long White NN155A, 2-branched stigma spreading 2.5 mm wide, Greyed Purple 187A; stamen 4.5 mm long, filaments 2 mm long and White NN155B, anthers 2 mm long and Greyed Brown N199A, pollen slight, Yellow Orange 16A.

*Involucral bracts*.—In 4 leafy series, area grows to 40 mm wide and 10 mm deep, lobes lanceolate in shape, reflexed, grow to 11 mm long and 3 mm wide, Green N137A, margins strigose, tip acute, strigose on both sides.

*Receptacle*.—Grows to 8 mm wide and 24 mm deep, White NN155B.

*Bloom period*.—June through October in Canby, Oreg.

*Fragrance*.—Floral, sweet.

*Lastingness*.—Each inflorescence lasts about four weeks in Canby, Oreg.

Seeds: 3 mm long and 2.5 mm wide, oval, Brown 200C.

*Fertility*.—Low.

Disease and pests: No pests or diseases have been observed on plants grown under commercial conditions in Canby, Oreg. No resistances are known.

I claim:

1. A new and distinct *Echinacea* plant as herein illustrated and described.

* * * * *

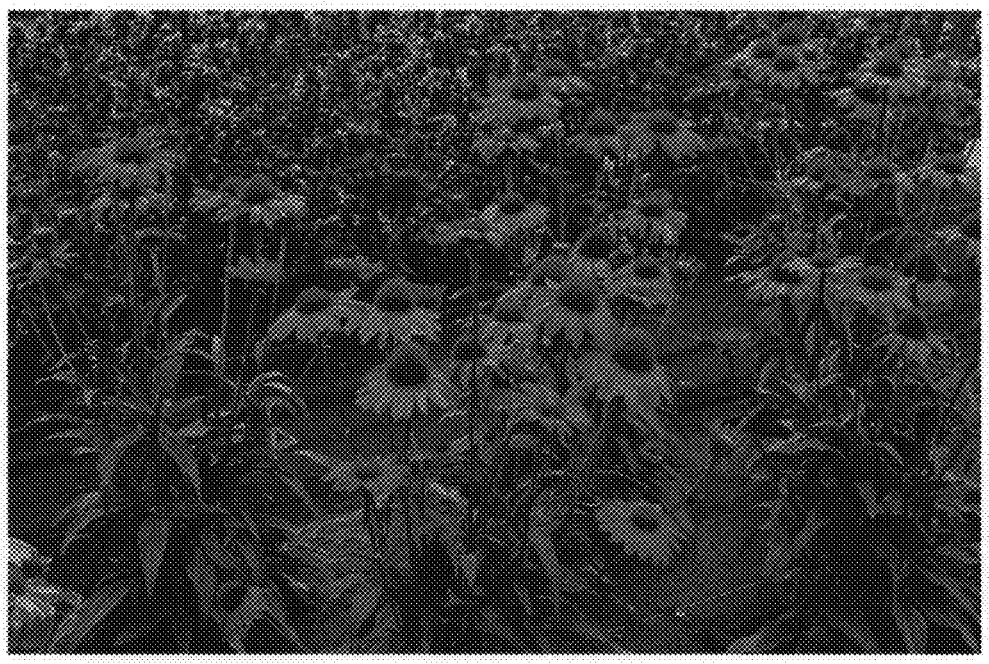

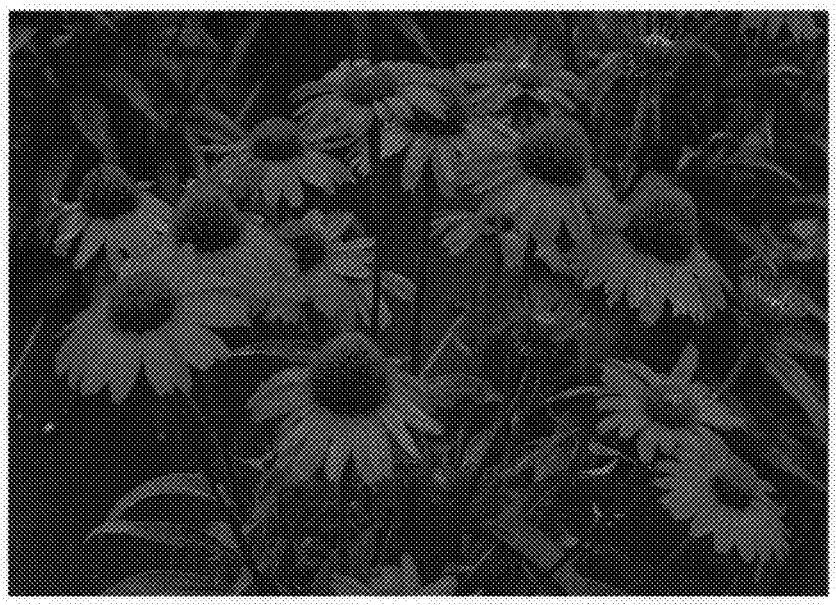
FIG. 1 above, FIG, 2 below